(12) United States Patent
Daftary et al.

(10) Patent No.: US 8,759,404 B2
(45) Date of Patent: Jun. 24, 2014

(54) INTRAVENOUS PROPOFOL EMULSION COMPOSITIONS HAVING PRESERVATIVE EFFICACY

(75) Inventors: Gautam Vinod Daftary, Mumbai (IN); Srikanth Annappa Pai, Mumbai (IN); Girish Narasimha Shanbhag, Mumbai (IN); Sangeeta Hanurmesh Rivankar, Mumbai (IN)

(73) Assignee: Bharat Serums & Vaccines Ltd., Mumbai (IN)

( * ) Notice: Subject to any disclaimer, the term of this patent is extended or adjusted under 35 U.S.C. 154(b) by 1803 days.

(21) Appl. No.: 11/714,061

(22) Filed: Mar. 2, 2007

(65) Prior Publication Data

US 2007/0249730 A1  Oct. 25, 2007

Related U.S. Application Data

(63) Continuation of application No. PCT/IN2006/000281, filed on Apr. 8, 2006.

(30) Foreign Application Priority Data

Aug. 5, 2005 (IN) .......................... 906/MUM/2005

(51) Int. Cl.
*A61K 31/05* (2006.01)

(52) U.S. Cl.
USPC ............ 514/731; 514/506; 514/553; 514/724

(58) Field of Classification Search
USPC .......................... 514/506, 553, 724, 730, 731
See application file for complete search history.

(56) References Cited

U.S. PATENT DOCUMENTS

| | | | |
|---|---|---|---|
| 4,067,997 A * | 1/1978 | Kabara | 514/552 |
| 5,714,520 A | 2/1998 | Jones et al. | |
| 6,028,108 A | 2/2000 | George | |
| 6,100,302 A | 8/2000 | Pejaver et al. | |
| 6,140,373 A | 10/2000 | May et al. | |
| 6,140,374 A | 10/2000 | May et al. | |
| 6,469,069 B1 | 10/2002 | Mirejovsky et al. | |
| 6,919,370 B2 | 7/2005 | Chen | |
| 2003/0073665 A1 | 4/2003 | Thompson et al. | |

FOREIGN PATENT DOCUMENTS

| | | |
|---|---|---|
| WO | WO 96/29064 | 9/1996 |
| WO | WO 99/39696 | 8/1999 |
| WO | WO 00/24376 | 5/2000 |
| WO | WO 00/59471 | 10/2000 |

OTHER PUBLICATIONS

Han et al., Physical properties and stability of two emulsion formulations of propofol, International Journal of Pharmaceutics, 2001, 207-220, 215.
Baker et al., Sulfite Supported Lipid Peroxidation in Propofol Emulsions, Anesthesiology, 2002, 1162-1167, 97.
Trapani et al; Inclusion Complexation of Propofol with 2-Hydroxypropyl-β-cyclodextrin. Physicochemical, Neuclear Magnetic Resonance Spectroscopic Studies, and Anesthetic Properties in Rat; J. Pharm. Sci; 1998; pp. 514-518; vol. 87, No. 4.
MacKenzie; Formulation and Evaluation of a Propanidid Hydroxypropyl-β-cyclodextrin Solution for Intravenous Anaesthesia; Int. J. Pharm; 1997; 191-196; vol. 159.
Trapani et al.; Propofol in Anesthesia. Mechanism of Action, Structure-Activity Relationships and Drug Delivery; Current Medicinal Chemistry; 2000; pp. 249-271; vol. 7.

\* cited by examiner

*Primary Examiner* — Sreeni Padmanabhan
*Assistant Examiner* — Shobha Kantamneni
(74) *Attorney, Agent, or Firm* — Thorpe North & Western LLP

(57) ABSTRACT

The invention discloses a stable intravenous Propofol oil-in-water emulsion composition having mixed preservatives of low toxicity that is capable of withstanding accidental contamination of bacteria and fungi. The preservative system employed comprising of monoglyceryl ester of lauric acid (Monolaurin) and a member selected from (a) capric acid and/or its soluble alkaline salts or its monoglyceryl ester (Monocaprin); (b) edetate; and (c) capric acid and/or its soluble alkaline salts or its monoglyceryl ester (Monocaprin) and edetate.

34 Claims, No Drawings

INTRAVENOUS PROPOFOL EMULSION COMPOSITIONS HAVING PRESERVATIVE EFFICACY

The present application is a continuation of PCT International Patent Application No. PCT/IN06/00281, filed on Apr. 8, 2006, which claims the benefit of India Patent Application No 906/MUM/2005, filed on Aug. 5, 2005, each of which is incorporated herein by reference.

FIELD OF INVENTION

The present invention relates to stable Propofol oil-in-water emulsion compositions for intravenous administration having preservative efficacy.

BACKGROUND AND PRIOR ART

Propofol is a short-acting intravenous anesthetic agent used for the induction of general anesthesia in adult patients and pediatric patients older than 3 years of age; maintenance of general anesthesia in adult patients and pediatric patients older than 2 months of age; and intensive care unit (ICU) sedation for intubated, mechanically ventilated adults. 20 ml ampoule of 1% propofol emulsion.

Initial clinical trials were in 1977, in a form solubilized in cremophor EL, but due to anaphylactic reactions it was withdrawn from the market. It was subsequently reformulated as an aqueous emulsion in intralipid and re-launched in 1986 by AstraZeneca with the brand name "Diprivan". The current preparation is 1% propofol solubilized in 10% soybean oil and contains 1.2% purified egg phospholipid, 2.25% glycerol and has a pH between 6.0 and 8.5 and a pKa of 11. Diprivan contains EDTA as an antimicrobial agent. Newer generic formulations contain sodium metabisulfite or benzyl alcohol.

Propofol is approved for the induction and maintenance of anesthesia in more than 50 countries.

Aside from the hypotension and transient apnea following induction doses, one of its most frequent side-effects is pain on injection, especially in smaller veins. This pain can be mitigated by pretreatment or mixing with intravenous lidocaine. Alternative formulations with a larger proportion of medium-chain triglycerides (as opposed to Intralipid) appear to have less pain on injection, possibly due to lower concentrations of free aqueous propofol. (Source: Wikipedia)

Propofol injections usually are made by diluting Propofol in oils and then formulated into oil-in-water type of emulsions. The compositions of the Propofol incorporated into the oily phase and made into oil-in-water emulsions for intravenous administration.

A Propofol/soybean oil emulsion has gained widespread use for induction and/or maintenance of anaesthesia, for maintenance of monitored anaesthesia care and for sedation in the Intensive Care Unit (ICU). It is advantageous in that it possesses both a rapid onset anaesthesia and a short recovery time. However, the presence of vegetable oils and phospholipids makes the emulsion highly prone to the risk of microbial growth.

Intravenous Propofol emulsion compositions are being increasingly used for sedation of seriously ill patients particularly in ICUs wherein it is continuously infused. There are noscomial (i.e. hospital acquired) infections observed very often in ICU patients. Hence it is recommended that the intravenous administration sets are changed frequently, at least every 6 or 12 hours. Continuous infusion makes the product susceptible to microbial growth.

In order to reduce the risk of uncontrolled microbial growth, additions of various potential preservatives into intravenous Propofol emulsion compositions have been tried. Some of the potential agents found to cause instability of the emulsion. Other potential agents failed to provide the level of antimicrobial activity being sought. It is necessary to preserve the compositions with preservatives that would provide the required levels of antimicrobial activity at as low a concentration as possible in order to minimize the potential for physical instability and to minimize toxicity concerns.

EP-A-0814787 (published 7 Jan. 1998; corresponding to U.S. Pat. No. 5,714,520, issued 3 Feb. 1998) discloses an oil-in-water emulsion of Propofol containing an edetate as an antimicrobial agent. The amount of edetate is preferably no more than 0.1% by weight but is sufficient to prevent a no more than 10 fold increase in the growth of each of *staphylococcus aureus* (ATCC 6538) *Eschericha coli* (ATCC 8739), *Pseudomonas aeruginosa* (ATCC9027), and *Candida albicans* (ATCC 10231) for at least 24 hours as measured by a test wherein a washed suspension of each organism is added to a separate aliquot of said composition at approximately 50 to 250 colony-forming units per ml at a temperature in the range 20-25° C., incubated in that temperature range and tested for viable counts of said organism after 24 hours. The currently marketed formulation comprises 1% w/v Propofol, 10% w/v Soybean Oil, 1.2% w/v Egg Phosphatides as an emulsifier, 2.25% w/v Glycerol and 0.0055% w/v disodium edetate, Sodium hydroxide and Water for Injection.

Edetate has been shown to delay but not to prevent the onset of microbial growth in Propofol emulsions (see WO-A-00/24376, infra). Propofol emulsion compositions are required to be diluted up to 5 times (1:4) for long-term infusion. On dilution the edetate concentration gets reduced to 0.0011%. Edetate alone is found to be ineffective in preventing a no more than 10 fold increase in broad-spectrum microbial growth at concentrations of 0.0025% and below (see U.S. Pat. No. 6,028,108; infra).

WO-A-99/39696 (published 12 Aug. 1999; corresponding to U.S. Pat. No. 6,469,069 issued 22 Oct. 2002) discloses an oil-in-water emulsion of Propofol containing a sulphite as an antimicrobial agent. The amount of sulphite preferably is in the range 0.0075% to 0.66% by weight and is sufficient to prevent a no more than 10 fold increase in the growth of each of *staphylococcus aureus* (ATCC 6538) *Eschericha coli* (ATCC 8739), *Pseudomonas aeruginosa* (ATCC9027), and *Candida albicans* (ATCC 10231) for at least 24 hours as measured by a test wherein a washed suspension of each organism is added to a separate aliquot of said composition at approximately 50 to 250 colony-forming units per ml and incubated at a temperature in the range 30-35° C. and tested for viable counts of said organism after 24 hours. The use of sulphite has two problems; viz. (a) stability of the emulsion is affected and (b) it is potentially toxic material at little higher dose level.

Reference is made to the water-immiscible solvent of the oil-in-water emulsion being a mono-, di-, or triglyceride. The preferred amount of solvent is 5 to 25% by weight.

Infusion of preferred compositions is accordance with WO-A-99/39696/U.S. Pat. No. 6,469,069 at a rate of 50 µg/kg/min for 24 hours will result in sulphite concentrations approaching the toxic levels. Further, the compositions may cause allergic reactions because of the sulphite molecule and the compositions have been reported to be physically and chemically unstable on exposure (see Han J et al International Journal of Pharmaceutics 2001, 215(1-2):207-220 & Baker M T et al Anesthesiology 2002, 97(5): 1162-1167).

WO-A-00/24376 (published 4 May 2000; corresponding to U.S. Pat. No. 6,140,373 & U.S. Pat. No. 6,140,374, both issued 31 Oct. 2000) discloses an oil-in-water emulsion of Propofol containing an antimicrobial agent selected from (a) benzyl alcohol alone or, preferably, together with either sodium edetate or sodium benzoate and (b) benzethonium chloride. Preferably, the composition comprises Propofol 0.1-5.0% by wt.; vegetable oil, preferably soybean oil, 1-30% by wt; surfactant, preferably egg phosphatide, 0.2 to 2% by wt.; glycerol 2-3% by wt.; and antimicrobial agent selected from (i) benzyl alcohol 0.0175-0.9% by wt., (ii) benzyl alcohol 0.07-0.9% by wt and sodium edetate 0.005% by wt., (iii) benzethonium chloride 0.01% to 0.1% by wt. and, most preferably, (iv) benzyl alcohol 0.0175-0.9% by wt. and sodium benzoate 0.07% by wt.

Reference is made to the water-immiscible solvent of the oil-in-water emulsion being an ester of a medium or long chain fatty acid, exemplified as a mono-, di-, or triglyceride. The preferred amount of solvent is 10 to 20% by weight.

For long-term use, the antimicrobial agents such as benzyl alcohol and benzethonium chloride are not recommended, as they are toxic.

WO-A-00/59471 (published 12 Oct. 2000; corresponding to U.S. Pat. No. 6,100,302, issued 8 Aug. 2000) discloses intravenous anaesthetic Propofol emulsions having decreased levels of soybean oil, fats or triglycerides. The formulation preferably consists of phospholipid-coated microdroplets ranging from 160 to 200 nanometers in diameter. These microdroplets contain a sphere of Propofol dissolved in a solvent, such as vegetable oil, surrounded by a stabilizing layer of a phospholipid. It is reported that this formulation can safely provide sedation over extended periods of time and that the low oil concentration emulsion containing Propofol provides a stable oil-in-water emulsion and unexpectedly exhibits antimicrobial properties comparable to higher water immiscible solvent concentration emulsions containing preservatives.

Typically the composition in the above patent specification comprises from 0.1 to 5%, by weight, preferably 1% to 2% by weight, of Propofol. The water-immiscible solvent, preferably soybean oil, is suitably present in an amount that is from 0.1 to 3% and more suitably from 1 to 3% by weight of the composition. However, the reduction in the oil content makes the injection more painful because of free Propofol in the aqueous phase.

SUMMARY OF THE INVENTION

The present invention provides a sterile, stable pharmaceutical oil-in-water emulsion composition of Propofol for intravenous administration having a preservative system which overcomes the drawbacks of prior art compositions.

More particularly the present invention is to provide oil-in-water emulsion compositions of Propofol having preservative efficacy to the extent that there will be no more than 10 fold increase for at least 24 hours in growth of each of *Pseudomonas aeruginosa, Escherichia coli, Staphylococcus aureus* and *Candida albicans*, after adventitious extrinsic contamination.

In accordance with the present inventions a stable, intravenously administrable, propofol oil-in-water emulsion composition, comprising triglyceride oils; emulsifiers selected from purified and/or modified natural phosphatides; water; tonicity modifying agents; and preservative system comprising of monoglyceryl ester of lauric acid (Monolaurin) and a member selected from (a) capric acid and/or its soluble alkaline salts or its monoglyceryl ester (Monocaprin);
(b) edetate; and
(c) capric acid and/or its soluble alkaline salts or its monoglyceryl ester (Monocaprin) and edetate.

In the Propofol oil-in-water emulsion composition, the preservative system is present in a sufficient concentration to prevent a no more than 10-fold increase in growth of each of *Pseudomonas aeruginosa* (ATCC 9027), *Escherichia coli* (ATCC 8739), *Staphylococcus aureus* (ATCC 6538) and *Candida albicans* (ATCC 10231) for at least 24 hours after adventitious extrinsic contamination.

DETAILED DESCRIPTION OF THE INVENTION

A. Ingredients:

The ingredients used in the compositions disclosed in the present invention are described here. Common ingredients as water, sodium hydroxide solution are not described.

Propofol:

2,6-bis(1-methylethyl)-phenol or 2,6-diisopropylphenol CAS Number 2078-54-8; $C_{12}H_{18}O$; Mol. Wt. 178.273 Pharmacopoeia: Propofol complying with European Pharmacopoeial (Ph.Eur.) specifications can be used. The content of Propofol is 0.1-2% w/v of the composition, preferably 0.5-2% w/v, more preferably about 1-2% w/v and most preferably about 1% w/v or about 2% w/v of the emulsion composition.

Triglyceride Oils:

triglyceride oil is selected from vegetable triglyceride oils and/or synthetic triglyceride oils. Vegetable triglyceride oils are usual vegetable oils such as soybean oil, sesame oil, safflower oil, olive oil. The synthetic triglyceride oil typically is manufactured from a vegetable oil, which is chemically and/or physically modified and/or purified. MCT oil is a typical example of synthetic oil and is obtained from the fixed oil extracted from the hard, dried fraction of the endosperm of *Cocos nucifera* L. Hydrolysis of the fixed oil followed by distillation yields the required fatty acids, which are then re-esterified to produce MCT oil (Medium-chain Triglycerides) that are mainly glycerol esters of caproic ($C_6$), Caprylic ($C_8$), Capric ($C_{10}$) and lauric cid ($C_{12}$) in a ratio of approximately 2:55:42:1. (source: http://www.pdrhealth.com)

In general the triglyceride oil is not more than 30% w/v of the composition. Preferably, it is 5%-20% w/v of the composition, more preferably it is about 10% w/v of the composition. The present invention may also comprise any combination of one or more vegetable oils and/or synthetic oils. Soybean oil is the preferred vegetable oil used in the compositions of the present invention. Soybean oil used in these compositions is preferably refined, bleached, deodorized and preferably free of heavy metal contaminants. Soybean oil complying with specifications of European Pharmacopoeia (Ph.Eur.)/United States Pharmacopoeia (USP) is preferred.

Phosphatides:

In the oil-in water emulsion compositions of the present invention purified and/or modified natural phosphatide is used as an emulsifier for stabilization of the oil-in-water emulsion. The preferred natural phosphatide used is either purified egg lecithin or purified soya lecithin or a mixture thereof. More preferably the natural phosphatide used is purified egg lecithin. The amount of said purified natural phosphatide is 0.1%-3% w/v preferably it is about 1.2% w/v.

Phosphatides are well known for forming liposomes when hydrated with aqueous media. However they are not used in the present invention for forming liposomal compositions. They are employed in the present invention as emulsifier and for stabilizing the emulsion.

Tonicity Modifying Agents:

The composition of the present invention is made isotonic to blood by incorporating a suitable tonicity modifying agent such as Glycerin, Dextrose, or Mannitol. Glycerin is the preferred tonicity modifying agent.

Preservatives:

The preservative system used in the present invention comprises monoglyceryl ester of lauric acid (Monolaurin) and a member selected from
(a) capric acid and/or its soluble alkaline salts or its monoglyceryl ester (Monocaprin);
(b) edetate; and
(c) capric acid and/or its soluble alkaline salts or its monoglyceryl ester (Monocaprin) and edetate.

Monoglyceryl Ester of Lauric Acid (Monolaurin)

When one of the hydroxyl group of glycerol is esterified with fatty acids, it is called monoacylglycerol or monoglyceride. When one OH group at either end of glycerol molecule is esterified with lauric acid it forms 1-monoglyceryl ester of lauric acid (1-monolaurin). When OH group at the middle or $2^{nd}$ position of glycerol molecule is esterified with lauric acid it forms 2-monoglyceryl ester of lauric acid (2-monolaurin). Of these two monolaurins, 1-monolaurin is preferred as a preservative in the present invention. The term Monolaurin as used in this specification refers to all pharmaceutically acceptable glyceryl mono esters of lauric acid having molecular formula $C_{15}H_{30}O_4$ and a molecular weight of about 274.4 and it does not include ethoxylated or propoxylated monolaurins. Commercially available Monolaurin is also known by other names such as "rac-1-Lauroylglycerol", "1-Monododecanoyl-rac-glycerol", "1-Monolauroyl-rac-glycerol", "rac-Glycerol 1-laurate", and "DL-α-Laurin".

A mixture of 1 and 2 monoglycerides, or 2-monoglycerides of lauric acid are also Monolaurins. Monolaurin may contain some diglycerides of lauric acid. The extent of purity of Monolaurin is not crucial, it should be rich in $C_{12}$ (lauric) fatty acid but presence of small amounts of $C_{10}$, $C_{14}$ etc fatty acids are acceptable.

Monolaurin exhibits polymorphism α form, β' form and β form; they have been reported to have melting points of 44° C., 59.5° C. and 63° C. respectively. The form of Monolaurin used in this invention is not critical for its use in this invention.

Monolaurin when used in combination with capric acid or edetate or both capric acid and edetate fulfils the requirements of preventing significant growth of microorganisms for at least 24 hours in the event of adventitious extrinsic contamination as mentioned above. The requirements of the quantities may, to some extent, depend on the nature of the Monolaurin used and 1-monolaurin is preferred in this respect. Hence the quantities can not be sharply defined and word "about" is prefixed to such quantities.

Monolaurin is insoluble in aqueous media but is highly soluble in the so-called fat solvents such as chloroform, benzene, ethanol, or acetone. HLB value of Monolaurin is less than 10 and therefore it is suitable as an emulsifier or solubilizer only for making water-in-oil emulsions and not oil-in-water emulsions. It is used in small quantities in the present invention as a preservative and not as an emulsifier or as a solubilizer.

In rats when Monolaurin is administered orally, the $LD_{50}$ has been reported to be about 53,000 mg/kg body weight.

Capric Acid:

Capric acid is a saturated fatty acid containing $C_{10}$ carbon atom naturally found in oils and fats. Capric acid is also known as Decanoic acid—CAS No. 334-48-5 having Molecular formula $C_{10}H_{20}O_2$ and Molecular weight 172.27. Capric acid has better anti-fungal properties than monolaurin. Oral $LD_{50}$ in rats is more than 10,000 mg/kg.

Purified capric acid is preferred. However, presence of small amounts of $C_8$ or $C_{12}$ or $C_{14}$ or such fatty acids are acceptable.

When used in Propofol compositions, when pH is adjusted with sodium hydroxide, capric acid sodium salt may be formed, being ionisable water soluble salt, it acts like capric acid. Alternately sodium caprate i.e. sodium salt of capric acid can also be used to provide required amount of capric acid which will also control the pH.

Salts of Capric Acid:

Any pharmaceutically acceptable soluble alkaline salts are useful. Sodium salt is preferred.

Sodium salt of Capric acid is soluble in water and has a molecular weight of $CH_3(CH_2)_8COONa$ and is commonly known as Sodium decanoate.

Monoglyceryl Ester of Capric Acid (Monocaprin):

Monoglyceryl esters of capric acid-monocaprate (monocaprin) can also be used to provide capric acid requirements, but free capric acid is preferred. Monocaprin is the monoglyceryl ester of Capric acid. When one hydroxyl group of glycerol is esterified with capric acid at 1-hydroxyl or 3-hydroxyl group, 1-monocaprin is obtained. Glycerol when esterified with capric acid at 2-hydroxyl group of glyercol, 2-monocaprin is obtained. Though either of the monocaprin is useful, in this invention, 1-monocaprin is preferred.

The amount of capric acid salts or monoglycerl ester of capric acid (monocaprin) are expressed as Capric acid in the specification.

Edetate:

Edetate whenever referred in this specification it includes ethylenediamine tetraacetic acid and derivatives thereof. Disodium edetate is the preferred edetate in this invention, however, presence of small amounts of other salts such as tetra sodium salt are acceptable.

Edetate is a metal chelating agent and used as a preservative in low concentration. The triglyceride oils used in this Propofol emulsion are contaminated with the trace amounts of metals, which deactivate the preservatives. Edetate helps to chelate the metal contaminants in the oil and thereby increase the efficiency of the preservatives.

For quantitative aspects edetate is expressed as Disodium edetate which has a molecular formula $C_{10}H_{16}N_2O_8Na_2$, CAS No. 6381-92-6. Oral $LD_{50}$ in rats is 2000 mg/kg.

Edetate concentration used in the composition of present invention itself is not sufficient to make it act as a preservative (see U.S. Pat. No. 6,028,108A). Not bound by theory, we believe that the minor quantity of edetate helps to boost the preservative activity of Monolaurin.

B. The Propofol Composition:

The propofol oil-in-water emulsion composition, with the ingredients of the preservative used in combination with other ingredients of the composition in the present invention make the composition sufficiently effective in preventing a no more than 10 fold increase in the growth of microbial cultures each of *Candida albicans* ATCC 10231, *Pseudomonas aeruginosa* ATCC 9027, *Escherichia coli* ATCC 8739 and *Staphylococcus aureus* ATCC 6538 for at least 24 hours after inoculation, and provide a stable, intravenously administrable composition.

The compositions of the present invention can also be made as a concentrate containing higher quantities of Propofol and then appropriately diluted for example with Dextrose solution.

Some preferred compositions of the present invention are given in Table 1.

TABLE 1

Propofol oil-in-water emulsion composition
Quantity (% w/v)

| Ingredients | Composition No. | | | | | |
| --- | --- | --- | --- | --- | --- | --- |
| | i | ii | iii | iv | v | vi |
| Propofol | 1 | 1 | 1 | 1 | 1 | 1 |
| Soybean oil | 10 | 10 | 10 | 10 | 10 | 10 |
| Purified egg lecithin | About 1.2 | About 1.2 | About 1.2 | About 1.2 | About 1.2 | About 1.2 |
| Glycerin | About 2.25 | About 2.25 | About 2.25 | About 2.25 | About 2.25 | About 2.25 |
| Monolaurin | 0.05 | 0.025 | 0.05 | 0.05 | 0.025 | 0.05 |
| Capric acid | 0.05 | — | 0.05 | 0.025 | 0.05 | 0.025 |
| Disodium edetate | — | 0.0025 | 0.001 | 0.0025 | 0.001 | 0.001 |
| Sodium hydroxide solution* | Sufficient to bring the pH between 5 and 8.5 | | | | | |
| Water for Injection | To make up to 100% by volume | | | | | |

*The intravenously administrable composition of the invention has a pH of 5-8.5 and preferably 6-8.5, conveniently adjusted by the presence of a relevant amount of alkali for example sodium hydroxide. Alternatively sodium salt of capric acid alone or in combination with alkali can also be used for adjustment of pH.

It should be noted that the quantities of Propofol, oil, emulsifier, may be varied within the limits as said above in the description of the ingredients, the combinations of the preservatives are equally important. For example, Propofol can be 0.1-2% w/v of the composition; triglyceride oil can be up to 30% w/v of the composition and purified and/or modified natural phosphatides can be 0.1-3% w/v of the composition. Some useful variations in ingredients of the preservative system in association with these other ingredients including tonicity modifying agents are shown in Table 2.

C. Compositions of the Preservative Systems

The preservative systems utilized in the Propofol oil-in-water emulsion compositions of the present invention comprise monoglyceryl ester of lauric acid (Monolaurin) and a member selected from
(a) capric acid and/or its soluble alkaline salts or its monoglyceryl ester (Monocaprin);
(b) edetate; and
(c) capric acid and/or its soluble alkaline salts or its monoglyceryl ester (Monocaprin) and edetate.

The concentration of the individual preservatives in the final composition will vary depending on the particular combination of the preservatives employed. Such combinations have not been taught as preservative systems useful in Propofol oil-in-water emulsion, or any other oil-in-water emulsions.

A particularly preferred amount of the individual ingredients in the preservative system of the present invention are summarized in Table 2.

TABLE 2

Compositions of Preservative System

| Components | Broad Range | Preferred Range | Most Preferred Range |
| --- | --- | --- | --- |
| (a): Monolaurin + Capric acid; (Disodium edetate - Nil) Amounts in % w/v of the final Propofol emulsion composition | | | |
| Monolaurin | 0.001-0.1% | 0.01-0.05% | About 0.05% |
| Capric acid | 0.001-0.1% | 0.01-0.05% | About 0.05% |
| (b): Monolaurin + Disodium Edetate; (Capric acid - Nil) Amounts in % w/v of the final Propofol emulsion composition | | | |
| Monolaurin | 0.001-0.1% | 0.01-0.05% | About 0.05% |
| Disodium edetate | 0.001-0.0025% | About 0.0025% | About 0.0025% |
| (C): Monolaurin + Capric acid + Disodium edetate Amounts in % w/v of the final Propofol emulsion composition | | | |
| Monolaurin | 0.001-0.1% | 0.01-0.05% | About 0.025% |
| Capric acid | 0.001-0.1% | 0.01-0.05% | About 0.025% |
| Disodium edetate | 0.001-0.0025% | About 0.0025% | About 0.0025% |

TABLE 3

Some Compositions of Preservative System
Amounts in % w/v of the final Propofol emulsion composition

| | Compositions | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| Monolaurin | 0.05 | 0.025 | 0.05 | 0.025 | 0.05 | 0.05 | 0.025 | 0.025 | 0.05 | 0.05 | 0.1 | 0.05 |
| Capric acid | 0.05 | 0.025 | — | — | 0.05 | 0.025 | 0.05 | 0.025 | 0.025 | 0.025 | 0.025 | — |
| Disodium edetate | — | — | 0.0025 | 0.0025 | 0.001 | 0.0025 | 0.001 | 0.0025 | — | 0.001 | — | 0.001 |

Thus, besides variations in quantities of Propofol oil-in-water emulsion ingredients like Propofol, triglyceride oil, phosphatide, variations in composition of the preservative system are many. Some preferred variations are i) The preservative system comprises monoglyceryl ester of lauric acid 0.001-0.1% w/v and capric acid and/or its soluble alkaline salts or its monoglyceryl ester (Monocaprin) expressed as capric acid 0.001%-0.1% w/v of the emulsion composition and edetate expressed as disodium edetate nil.

ii) Another preservative system comprises monoglyceryl ester of lauric acid 0.025-0.1% w/v and capric acid and/or its soluble alkaline salts or its monoglyceryl ester (Monocaprin) expressed as capric acid 0.025%-0.1% w/v and edetate expressed as disodium edetate 0.001%-0.0025% w/v of the emulsion composition.

(Monocaprin) expressed as capric acid 0.025%-0.1% w/v and edetate expressed as disodium edetate about 0.001% w/v of the emulsion composition.

It may be noted that the preservative systems (c) all the three ingredients represented by Monolaurin, Capric acid and Edetate are present as said above. In the preservative system (a) Edetate is absent and in preservative system (b) capric acid is absent.

D. The Process of Preparing Emulsion Composition

The process of preparing an intravenously administrable Propofol oil-in-water emulsion composition of the present invention was studied to see if different modes of incorporating the preservative system would give any advantageous method. Such combinations are shown in Table 4. Such process variation has been described in Example I (infra) for a typical Propofol oil-in-water emulsion composition.

TABLE 4

Modes of incorporating preservative system in oil-in-water emulsion.

| Preservative system | Aqueous phase | Oily phase |
| --- | --- | --- |
| Monolaurin + Capric acid | Monolaurin | Capric acid |
| | Capric acid | Monolaurin |
| | Capric acid + Monolaurin | — |
| | — | Capric acid + Monolaurin |
| | Capric acid + Monolaurin | Capric acid + Monolaurin |
| | Capric acid + Monolaurin | Monolaurin |
| | Capric acid + Monolaurin | Capric acid |
| | Monolaurin | Capric acid + Monolaurin |
| | Capric acid | Capric acid + Monolaurin |
| Monolaurin + Disodium Edetate | Monolaurin + Disodium edetate | — |
| | Disodium edetate | Monolaurin |
| | Monolaurin + Disodium edetate | Monolaurin |
| Monolaurin + Capric acid + Disodium Edetate | Monolaurin + Disodium Edetate | Capric acid |
| | Capric acid + Disodium Edetate | Monolaurin |
| | Capric acid + Monolaurin + Disodium Edetate | — |
| | Disodium Edetate | Capric acid + Monolaurin |
| | Capric acid + Monolaurin + Disodium Edetate | Capric acid + Monolaurin |
| | Capric acid + Monolaurin + Disodium Edetate | Monolaurin |
| | Capric acid + Monolaurin + Disodium Edetate | Capric acid |
| | Monolaurin + Disodium Edetate | Capric acid + Monolaurin |
| | Capric acid + Disodium Edetate | Capric acid + Monolaurin | iii) Another preservative system comprises monoglyceryl ester of lauric acid about 0.05% w/v and capric acid and/or its soluble alkaline salts or its monoglyceryl ester (Monocaprin) expressed as capric acid 0.025%-0.1% w/v and edetate expressed as disodium edetate 0.001%-0.0025% w/v of the emulsion composition.

iv) Another preservative system comprises monoglyceryl ester of lauric acid 0.025-0.1% w/v and capric acid and/or its soluble alkaline salts or its monoglyceryl ester (Monocaprin) expressed as capric acid about 0.025% w/v and edetate expressed as disodium edetate 0.001%-0.0025% w/v of the emulsion composition.

v) Another preservative system comprises monoglyceryl ester of lauric acid 0.025-0.1% w/v and capric acid and/or its soluble alkaline salts or its monoglyceryl ester (Monocaprin) expressed as capric acid 0.025%-0.1% w/v and edetate expressed as disodium edetate about 0.0025% w/v of the emulsion composition.

vi) Another preservative system comprises monoglyceryl ester of lauric acid 0.025-0.1% w/v and capric acid and/or its soluble alkaline salts or its monoglyceryl ester The compositions containing each of the above preservative system could be prepared by different processes wherein the phosphatide is incorporated into either aqueous phase or oily phase or partly into aqueous phase and partly into oily phase.

In the process of present invention, the tonicity-modifying agent is incorporated into the aqueous phase. The pH of the aqueous phase is suitably adjusted before adding the oily phase to it. Alternatively the pH of the emulsion is suitably adjusted either before homogenisation or after homogenisation.

It is also possible to add the mixture of preservative system to a preformed emulsion. In such instances Monolaurin is dispersed in small quantity of water (1 in 10) at 55° C.-60° C. This is mixed well and added to preformed emulsion under stirring. Capric acid is preferably added to a preformed emulsion under stirring after melting in a water bath (30° C.-35° C.).

In the aforementioned process aspects, it is preferred that: the homogenisation is carried out to an average globule size of less than 500 nanometers; the homogenized composition is filtered; the resultant filtrate is filled into containers, followed by nitrogen blanketing and the filled containers sealed; and the said filtrate in the sealed containers is sterilized by autoclaving.

A process for the preparation of the Propofol oil-in-water emulsion compositions of the present invention is described below:
i) preparing oil phase in triglyceride oil maintained at about 75° C., by adding Propofol;
ii) preparing an aqueous phase in water at about 70° C.; by adding glycerol and sodium hydroxide solution to make it alkaline;
iii) adding the emulsifier and individual ingredients of the preservative system of claim 1 in the oil phase either totally or partly and adding the remaining in the aqueous phase;
iv) adding said oily phase obtained at step i) to said aqueous phase obtained at step ii) under stirring to produce a coarse emulsion;
v) homogenizing the said coarse emulsion obtained at step iv) to an average globule size of less than 500 nanometers;
vi) filtering the said composition obtained at the end of step v);
vii) filling the said filtrate obtained at the end of step vi) in containers such as vials, ampoules, under nitrogen blanketing and sealing the filled containers;
viii) sterilizing said filtrate in said sealed containers by autoclaving.

Another process for the preparation of the Propofol oil-in-water emulsion compositions of the present invention is described below:
i) preparing oil phase in triglyceride oil maintained at about 75° C., by dissolving Propofol and the emulsifier;
ii) preparing an aqueous phase in water at about 70° C.; by adding glycerol, sodium hydroxide solution;
iii) adding said oily phase obtained at step i) to said aqueous phase obtained at step ii) under stirring to produce a coarse emulsion;
iv) homogenizing the said coarse emulsion obtained at step iii) to an average globule size of less than 500 nanometers;
v) adding the chosen preservative system as claimed in any preceding claim;
vi) filtering the said composition obtained at the end of step v);
vii) filling the said filtrate obtained at the end of step vi) in containers such as vials, ampoules, under nitrogen blanketing and sealing the filled containers;
viii) sterilizing said filtrate in said sealed containers by autoclaving.

EXAMPLES

The invention will now be illustrated by way of Examples. The Examples are by way of illustration only and in no way restrict the scope of the invention.

Materials and equipment used in the Examples:
Propofol complies with the European Pharmacopoeia (Ph.Eur.) specifications, Glycerin, Sodium hydroxide, Water for Injection complies with Indian Pharmacopoeia (I.P.)/Ph.Eur. specifications.
Soya oil (Soybean oil) complies with Ph.Eur./U.S.P. specifications.
Purified egg lecithin (referred to as Egg lecithin in examples) is manufactured by M/s.Lipoid.
Monolaurin is a racemic mixture obtained from Sigma/M/s. Lipoid.
Capric acid is obtained from Sigma.
Sodium decanoate is obtained from Sigma
Disodium edetate used complies with Pharmacopoeial specifications.
High speed mixing was done using a laboratory Remi stirrer. Emulsions were homogenized using high pressure APV homogenizer. The batch size of the Propofol oil-in-water emulsion compositions illustrated in Examples are in 300 mL quantities.

Examples IA, IB, IC and ID

Propofol Oil-In-Water Emulsion Compositions Containing Preservatives Monolaurin and Capric Acid The composition of Example I as shown in Table 5 was prepared by 4 different processes as Examples IA, IB, IC, and ID.

TABLE 5

Composition of Example I

| Ingredients | % w/v |
| --- | --- |
| Propofol | 1 |
| Soybean oil | 10 |
| Purified egg lecithin | About 1.2 |
| Glycerin | About 2.25 |
| Monolaurin | 0.025 |
| Capric acid | 0.025 |
| Disodium edetate | — |
| Sodium hydroxide | q.s.* |
| Water | q.s. 100% |

*for adjusting pH

Example IA

Preparation of Oil Phase

Soya oil was heated to 70-75° C., Capric acid and Propofol were added and mixed.

Preparation of Aqueous Phase

To Water for Injection, add Glycerin followed by Monolaurin and stir to dissolve. Purified egg lecithin was added and dispersed in the aqueous phase. The pH was then adjusted to 10.5 with sodium hydroxide solution.

Emulsification

The Oil Phase was added to the Aqueous Phase with mixing and stirred at high-speed for about 10 minutes to get a coarse emulsion.

The coarse emulsion was then homogenized and the average globule size obtained was less than 500 nanometers.

The emulsion was filtered, filled in U.S.P. Type I vials and sealed after blanketing with Nitrogen gas. The vials were then sterilized by autoclaving.

Example IB

Similar to Example IA. However, Purified egg lecithin was added in the oily phase.

Example IC

Similar to Example IA. However, half the quantity of Purified egg lecithin was added in the oily phase and half of the quantity was added in the aqueous phase.

Example ID

Similar to Example IA. However, Monolaurin was dissolved in the oily phase and Capric acid was dissolved in aqueous phase.

Example IIA

Samples of Examples IA, IB, IC, and ID were examined for globular size, and Propofol and degradation products content by the methods given below:
1. Globule size: Globule size is determined using N4-Plus instrument from Coulter Counter.
2. Propofol and degradation products content: Propofol and degradation products content was determined by HPLC. The details are as follows:

| | |
|---|---|
| Column | Hypersil ODS |
| Detector | Ultraviolet detector |
| Detection wavelength | 270 nm |
| Mobile phase | 60:15:25 Acetonitrile:methanol:10 mM potassium phosphate Buffer |
| Sample concentration | 0.2 mg/ml |
| Flow rate | 1 ml/min. |

Example IIB

The compositions of Examples IA, IB, IC and ID were analysed and the analytical data of the compositions obtained as shown Table 6:

TABLE 6

| | | Example I | | | |
|---|---|---|---|---|---|
| Tests | | IA | IB | IC | ID |
| Appearance | | WOL | WOL | WOL | WOL |
| pH | | 6.98 | 6.8 | 6.83 | 8.2 |
| Propofol content (mg/mL) | | 10.16 | 10.15 | 10.41 | 10.17 |
| Degradation products (% of Propofol content) | Benzo-quinone | 0.02 | 0.02 | 0.02 | 0.01 |
| | Bis-propofol | 0.15 | 0.043 | 0.044 | 0.17 |
| AverageGlobule Size (μm) | | 0.18 | 0.19 | 0.20 | 0.19 |

WOL—White opaque liquid.

Compositions of Example IA, IB, IC, and ID were tested for determining preservative activity using the procedure as described in Example III.

Example III

Determination of Preservative Activity of Samples of Example IA, IB, IC, and ID

Procedure for Determination of Preservative Efficacy

Approximately 50 to 250 colony forming units (cfu) per ml of each of *Candida albicans* ATCC 10231, *Pseudomonas aeruginosa* ATCC 9027, *Escherichia coli* ATCC 8739 and *Staphylococcus aureus* ATCC 6538, the four standard U.S.P. organism cultures specified under "Antimicrobial Effectiveness Testing" were added to a separate aliquot of the product and incubated at $22\pm2°$ C. (for fungal cultures) and $32°$ C.$\pm2°$ C. (for bacterial cultures). The viable counts of the test organisms were determined after 24 hours and 48 hours.

Method of Determination of Preservative Efficacy for Fungal Culture
1. Inoculate the test samples with 0.1 ml of $1:10^3$ diluted suspension of standard culture of *C. albicans*, such that the inoculated test samples contain 50 to 250 cfu/ml.
2. Incubate the test samples for 24 hours at $22°$ C.$\pm2°$ C.
3. Determine the cell density inoculated into the test samples by the Surface spread method.
4. After 24-hour incubation of the test samples, carry out 3 ten-fold serial dilution of the test samples.
5. Surface-spread 0.1 ml of the test samples (undiluted) along with the 3 ten-fold serial dilution tubes onto sterile Sabouraud Dextrose Agar Petri plates.
6. Incubate the Petri plates for 48 hours at $22°$ C.$\pm2°$ C.
7. Count the number of colonies per plate and determine the cell density in the test samples (after 24-hour of inoculation).
8. Similarly after 48-hour incubation of the test samples, carry out 3 ten-fold serial dilution of the test samples, surface-spread 0.1 ml of the test samples onto sterile Sabouraud Dextrose Agar Petri plates, incubate for 48 hours at $22°$ C.$\pm2°$ C. and determine the cell density in the test samples (after 48-hour of inoculation).

Not more than ten-fold increase in the cell counts in the test samples indicate preservative efficacy of the test samples.

Method of Determination of Preservative Efficacy for Bacterial Cultures
1. Inoculate the test samples with 0.1 ml of $1:10^3$ diluted suspension, such that the inoculated test samples contain 50 to 250 cfu/ml
2. Incubate the test samples for 24 hours at $32°$ C.$\pm2°$ C.
3. Determine the cell density inoculated into the test samples by the Surface spread method.
4. After 24-hour incubation of the test samples, carry out 3 ten-fold serial dilution of the test samples.
5. Surface-spread 0.1 ml of the test samples (undiluted) along with the 3 ten-fold serial dilution tubes onto sterile Soyabean-Caesin Agar Petri plates.
6. Incubate the Petri plates for 24 hours at $32°$ C.$\pm2°$ C.
7. Count the number of colonies per plate and determine the cell density in the test samples (after 24-hour of inoculation).
8. Similarly after 48-hour incubation of the test samples, carry out 3 ten-fold serial dilution of the test samples, surface-spread 0.1 ml of the test samples onto sterile Soyabean-Caesin Agar Petri plates, incubate for 24 hours at $32°$ C.$\pm2°$ C. and determine the cell density in the test samples (after 48-hour of inoculation).

Efficacy of Preservative System Tested:

Compositions of the Example I A, IB, IC and ID showed no more than 10-fold growth at the end of 24 hours.

Example IV-IX

Compositions of Examples IV-IX as given in Table 7

TABLE 7

Propofol oil-in-water emulsion compositions

| | Examples | | | | | Quantity/100 ml |
|---|---|---|---|---|---|---|
| | IV | V | VI | VII | VIII | IX |
| Propofol | 1 g | 1 g | 1 g | 1 g | 1 g | 1 g |
| Monolaurin | 0.05 g | 0.05 g | 0.05 g | 0.1 g | 0.025 g | 0.05 g |
| Capric acid | 0.025 g | — | — | 0.025 g | 0.025 g | 0.05 g |
| Soya Oil | 10 g | 10 g | 10 g | 10 g | 10 g | 10 g |
| Egg lecithin | 1.2 g | 1.2 g | 1.2 g | 1.2 g | 1.2 g | 1.2 g |
| Glycerin | 2.25 g | 2.25 g | 2.25 g | 2.25 g | 2.25 g | 2.25 g |
| Disodium edetate | — | 0.0025 g | 0.001 g | — | 0.0025 g | — |
| Sodium hydroxide(0.1N)* | q.s. | q.s. | q.s. | q.s. | q.s. | q.s. |
| Water for Injection | q.s. to 100 ml | q.s. to 100 ml | q.s. to 100 ml | q.s. to 100 ml | q.s. to 100 ml | q.s. to 100 ml |

*to adjust pH to 6-8.5

Example IV

Preparation of Oil Phase

Soya oil was heated to 70-75° C., Capric acid and Propofol were added and mixed.

Preparation of Aqueous Phase

To Water for Injection at 65-70° C. was added Glycerin followed by Monolaurin and stirred to dissolve. Purified egg lecithin was added and dispersed in the aqueous phase. The pH was then adjusted to 10.5 with sodium hydroxide solution.

Emulsification

The Oil Phase was added to the Aqueous Phase under stirring and mixed at high-speed for about 15 minutes to get a coarse emulsion. The coarse emulsion was then homogenized to get desired average globule size of less than 500 nanometers.

The emulsion was filtered, filled in U.S.P. Type I vials and sealed after blanketing with Nitrogen gas. The vials were then sterilized by autoclaving.

On analysis the product had the following composition:

| | |
|---|---|
| 1. Propofol content | 10.05 mg/mL |
| 2. Monolaurin content | 0.47 mg/mL |
| 3. Capric acid content | 0.26 mg/mL |
| 4. pH | 7.05 |
| 5. Average Globule size | 190 nm |

Example V

Preparation of Oil Phase

Soya oil was heated to 70-75° C., Monolaurin and Propofol were added and mixed.

Preparation of Aqueous Phase

To Water for Injection at 65-70° C. added Disodium edetate followed by Glycerin and stirred to dissolve. Purified egg lecithin was added and dispersed in the aqueous phase. The pH was then adjusted to 10.6 with sodium hydroxide solution.

Emulsification

The Oil Phase was added to the Aqueous Phase under stirring and mixed at high-speed for about 15 minutes to get a coarse emulsion.

The coarse emulsion was then homogenized to get desired average globule size of less than 500 nanometers.

The emulsion was filtered, filled in U.S.P. Type I vials and sealed after blanketing with Nitrogen gas. The vials were then sterilized by autoclaving.

Example VI

Preparation of Oil Phase

Soya oil was heated to 70-75° C., Monolaurin and Propofol were added and mixed.

Preparation of Aqueous Phase

To Water for Injection at 65-70° C. added Disodium edetate followed by Glycerin and stirred to dissolve. Purified egg lecithin was added and dispersed in the aqueous phase. The pH was then adjusted to 10.6 with sodium hydroxide solution.

Emulsification

The Oil Phase was added to the Aqueous Phase under stirring and mixed at high-speed for about 15 minutes to get a coarse emulsion. The coarse emulsion was then homogenized to get desired average globule size of less than 500 nanometers.

The emulsion was filtered, filled in U.S.P. Type I vials and sealed after blanketing with Nitrogen gas. The vials were then sterilized by autoclaving.

Example VII

Preparation of Oil Phase

Soya oil was heated to 70-75° C., Capric acid and half the quantity of Monolaurin along with Propofol were added and mixed. Added half the quantity of Egg lecithin and mixed well.

Preparation of Aqueous Phase

To Water for Injection at 65-70° C. added Glycerin followed by remaining quantity of Monolaurin and stirred to dissolve. Added remaining half quantity of Purified egg lecithin and dispersed in the aqueous phase. The pH was then adjusted to 10.5 with sodium hydroxide solution.

Emulsification

The Oil Phase was added to the Aqueous Phase under stirring and mixed at high-speed for about 15 minutes to get a coarse emulsion. The coarse emulsion was then homogenized to get desired average globule size of less than 500 nanometers.

The emulsion was filtered, filled in U.S.P. Type I vials and sealed after blanketing with Nitrogen gas. The vials were then sterilized by autoclaving.

On analysis the product had the following composition:

| | |
|---|---|
| 1. Propofol content | 9.98 mg/mL |
| 2. Monolaurin content | 0.91 mg/mL |
| 3. Capric acid content | 0.23 mg/mL |
| 4. pH | 8.02 |
| 5. Average Globule size | 198 nm |

Example VIII

Preparation of Oil Phase

Soya oil was heated to 70-75° C., Capric acid and Propofol were added and mixed.

Preparation of Aqueous Phase

To Water for Injection at 65-70° C. added Disodium edetate followed by Glycerin and Monolaurin. Stirred to dissolve. Purified egg lecithin was added and dispersed in the aqueous phase. The pH was then adjusted to 10.6 with sodium hydroxide solution.

Emulsification

The Oil Phase was added to the Aqueous Phase under stirring and mixed at high-speed for about 15 minutes to get a coarse emulsion. The coarse emulsion was then homogenized to get desired average globule size of less than 500 nanometers.

The emulsion was filtered, filled in U.S.P. Type I vials and sealed after blanketing with Nitrogen gas. The vials were then sterilized by autoclaving.

On analysis, the product had the following composition:

| | |
|---|---|
| 1. Propofol content | 9.89 mg/mL |
| 2. Monolaurin content | 0.270 mg/mL |
| 3. Capric acid content | 0.254 mg/mL |
| 4. pH | 7.96 |
| 5. Average Globule size | 190 nm |

Example IX

Preparation of Oil Phase

Propofol was added to Soya oil maintained at 70-75° C. Purified egg lecithin was added and mixed.

Preparation of Aqueous Phase

To Water for Injection at 65-70° C., added Glycerin. The pH was then adjusted to 10.5 with sodium hydroxide solution.

Emulsification

The Oil Phase was added to the Aqueous Phase under mixing to get a coarse emulsion. The coarse emulsion was then homogenized to get desired average globule size of less than 500 nanometers.

Addition of Preservatives

Required quantity of Monolaurin was dispersed in Water for Injection at 50° C.-55° C. and added to the bulk homogenized emulsion.

Capric acid was melted at 30° C.-35° C. in a water bath and required quantity added to the bulk homogenized emulsion. Mixed well.

The emulsion was filtered, filled in U.S.P. Type I vials and sealed after blanketing with Nitrogen gas. The vials were then sterilized by autoclaving.

The analytical data on the composition of Example IX is provided in Table 8:

TABLE 8

| | | |
|---|---|---|
| Appearance | | White opaque liquid |
| pH | | 6.60 |
| Propofol content (mg/mL) | | 9.89 |
| Degradation products (% of Propofol content) | Benzo-quinone | 0.067 |
| | Bis-propofol | 0.075 |
| Free Fatty Acids (mEq/L) | | <10 |
| Globule Size (μm) | | 0.20 |
| Monolaurin content (mg/mL) | | 0.47 |
| Capric acid content (mg/mL) | | 0.53 |
| Preservative efficacy | C. albicans | *2.0 × $10^2$   **1.3 × $10^3$ |
| | | Does not support growth |
| | E. coli | *9.3 × $10^1$   **1.5 × $10^1$ |
| | | Does not support growth |
| | P. aeruginosa | *1.7 × $10^2$   **5.5 × $10^1$ |
| | | Does not support growth |
| | S. aureus | *1.2 × $10^2$   **7.0 × $10^1$ |
| | | Does not support growth |

*Initial count
**Count at the end of 24 hours

Example X

Samples of Example IX was studied for Chemical stability and Stability of Preservative efficacy. The chemical stability observations at the end of 3 months at 40° C. and 25° C. are provided in Table 9 along with the preservative efficacy at the end of 10 weeks:

TABLE 9

| Tests | | 40° C.-3 Months | 25° C.-3 Months |
|---|---|---|---|
| Appearance | | White opaque liquid | White opaque liquid |
| pH | | 6.45 | 6.45 |
| Propofol content (mg/mL) | | 9.81 | 9.86 |
| Degradation products | Benzo-quinone | 0.067 | 0.065 |
| (% of Propofol content) | Bis-propofol | 0.100 | 0.078 |
| Free Fatty Acids (mEq/L) | | <10 | <10 |
| Globule Size (μm) | | 0.21 | 0.21 |
| Monolaurin content (mg/mL) | | 0.46 | 0.47 |
| Capric acid content (mg/mL) | | 0.51 | 0.52 |

| Test | | 40° C.-10 Weeks | 25° C.-10 Weeks |
|---|---|---|---|
| Preservative efficacy at the end of 10 weeks | C. albicans | *68 **65 DNSG | *68 **95 DNSG |
| | E. coli | *75 **<10 DNSG | *75 **55 DNSG |
| | P. aeruginosa | *69 **15 DNSG | *69 **10 DNSG |
| | S. aureus | *120 **130 DNSG | *120 **180 DNSG |

*Initial count
**Count at the end of 24 hours
DNSG—Does not support growth

All the Examples show that the degradation products of Propofol are within the acceptable limits on preparation and on storage for 3 months. The following method was followed for analyzing Monolaurin and Capric acid content:

Determination of Monolaurin and Capric Acid Content:

Monolaurin and Capric acid content were determined by HPLC. The details are as follows:

Chromatographic system:

The Liquid Chromatograph equipped with RI detector and 150 mm×4.6 mm×5μ, ODS Cosmosil, column. Maintain Column temperature at 35° C.±0.5° C.

Mobile Phase:

Methanol: Phosphate Buffer 80:20

Flow Rate:

1 mL/min.

Example XI

Determination of Preservative Activity

Compositions of Example IV to IX were tested for determining preservative activity using the following procedure:

Approximately 50 to 250 colony forming units (cfu) per ml of each of *Candida albicans* ATCC 10231, *Pseudomonas aeruginosa* ATCC 9027, *Escherichia coli* ATCC 8739 and *Staphylococcus aureus* ATCC 6538, the four standard U.S.P. organism cultures specified under "Antimicrobial Effectiveness Testing" were added to a separate aliquot of the product and incubated at 22±2° C. The viable counts of the test organisms were determined after 24 hours and 48 hours.

Not more than ten-fold increase in the cell counts in the test samples indicate preservative efficacy of the test samples.

The study carried out indicated that compositions of the Example IV to IX showed no more than 10-fold growth at the end of 24 hours.

Example XII

| | Quantity/100 ml |
|---|---|
| Propofol | 1 g |
| Monolaurin | 50 mg |
| Sodium decanoate | 56.5 mg |
| Soya Oil | 10 g |
| Egg lecithin | 1.2 g |
| Glycerin | 2.25 g |
| Sodium hydroxide(0.1N)* | q.s. |
| Water for Injection | q.s. to 100 ml |

Procedure of Example IX is followed except in the step of "Addition of preservatives", in place of Capric acid, weighed quantity of Sodium decanoate is dissolved in Water for Injection and added to the bulk homogenized emulsion. On analysis the composition was found to have Propofol 9.97 mg/mL, Average Globule size 210 nm and Sodium decanoate expressed as Capric acid 0.52 mg/mL.

It will be understood that the invention is not restricted to the specific details described above but that numerous modifications and variations can be made without departing from the teachings of the invention as disclosed in the specifications.

ADVANTAGES OF THE INVENTION

The Propofol oil-in-water compositions with preservative system of the present invention comprising monoglyceryl ester of lauric acid (Monolaurin) and a member selected from (a) capric acid and/or its esters or salts; (b) edetate; and (c) capric acid and edetate do not support microbial growth in case of accidental contamination.

The preservative system of the present invention having more than one preservative is safer than the earlier products using a single preservative such as editate, sodium metabisulfite or benzyl alcohol.

In another aspect the compositions of the present invention are stable than compositions using sulphites because of sulphites make the product physically and chemically unstable on long-term storage. Sulphites have been reported to support lipid peroxidation in Propofol emulsion and also cause allergic reactions on intravenous administration. Propofol oil-in-water emulsion compositions is better than the use of sulphites.

The invention claimed is:

1. A stable, intravenously administrable, propofol oil-in-water emulsion composition, comprising triglyceride oils in an amount of 1-30% (w/v); emulsifiers selected from purified natural phosphatides; water; tonicity modifying agents; and preservative system consisting essentially of monoglyceryl ester of lauric acid (monolaurin) in an amount of 0.001% (w/v) to 0.1% (w/v) and a member selected from the group consisting of
   (a) capric acid and/or its soluble alkaline salts or its monoglyceryl ester (monocaprin) in an amount of 0.001% (w/v) to 0.1% (w/v) when expressed as capric acid;
   (b) edetate in an amount of 0.001% (w/v) to 0.0025% (w/v) when expressed as disodium edetate; and (c) capric acid and/or its soluble alkaline salts or its monoglyceryl ester (mono caprin) in an amount of 0.001% (w/v) to 0.1% (w/v) when expressed as capric acid and edetate in an amount of 0.001% (w/v) to about 0.0025% (w/v) when expressed as disodium edetate.

2. Propofol oil-in-water emulsion composition as claimed in claim 1, wherein the preservative system prevents a no more than 10-fold increase in growth of each of *pseudomonas aeruginosa* (ATCC 9027), *escherichia coli* (ATCC 8739), *Staphylococcus aureus* (ATCC 6538) and *candida albicans* (ATCC 10231) for at least 24 hours after adventitious extrinsic contamination.

3. Propofol oil-in-water emulsion composition as claimed in claim 1 wherein, the preservative system consists essentially of monoglyceryl ester of lauric acid 0.025-0.1% w/v and capric acid and/or its soluble alkaline salts or its monoglyceryl ester (monocaprin) expressed as capric acid 0.025%-0.1% w/v and edetate expressed as disodium edetate 0.001%-0.0025% w/v of the emulsion composition.

4. Propofol oil-in-water emulsion composition as claimed in claim 1 wherein, the preservative system consists essentially of monoglyceryl ester of lauric acid about 0.05% w/v and capric acid and/or its soluble alkaline salts or its monoglyceryl ester (monocaprin) expressed as capric acid 0.025%-0.1% w/v and edetate expressed as disodium edetate 0.001%-0.0025% w/v of the emulsion composition.

5. Propofol oil-in-water emulsion composition as claimed in claim 3 wherein, the preservative system consists essentially of monoglyceryl ester of lauric acid 0.025-0.1% w/v and capric acid and/or its soluble alkaline salts or its monoglyceryl ester (monocaprin) expressed as capric acid about 0.025% w/v and edetate expressed as disodium edetate 0.001%-0.0025% w/v of the emulsion composition.

6. Propofol oil-in-water emulsion composition as claimed in claim 3 wherein, the preservative system consists essentially of monoglyceryl ester of lauric acid 0.025-0.1% w/v and capric acid and/or its soluble alkaline salts or its monoglyceryl ester (monocaprin) expressed as capric acid 0.025%-0.1% w/v and edetate expressed as disodium edetate about 0.0025% w/v of the emulsion composition.

7. Propofol oil-in-water emulsion composition as claimed in claim 3 wherein, the preservative system consists essentially of monoglyceryl ester of lauric acid 0.025-0.1% w/v and capric acid and/or its soluble alkaline salts or its monoglyceryl ester (monocaprin) expressed as capric acid 0.025%-0.1% w/v and edetate expressed as disodium edetate about 0.001% w/v of the emulsion composition.

8. Propofol oil-in-water emulsion composition as claimed in claim 1 wherein, the amount of propofol is 0.1%-2% w/v of the composition.

9. Propofol oil-in-water emulsion composition as claimed in claim 8 wherein, the amount of propofol is 0.5%-2% w/v.

10. Propofol oil-in-water emulsion composition as claimed in claim 9 wherein, the amount of propofol is about 1% w/v.

11. Propofol oil-in-water emulsion composition as claimed in claim 1 wherein, said triglyceride oil is selected from vegetable oils such as soybean oil, sesame oil, safflower oil, olive oil and/or synthetic triglyceride oils such as medium chain triglyceride (MCT) oil.

12. Propofol oil-in-water emulsion composition as claimed in claim 1 wherein, the amount of said triglyceride oil is 5%-20% w/v of the composition.

13. Propofol oil-in-water emulsion composition as claimed in claim 12 wherein, the amount of said triglyceride oil is about 10% w/v of the composition.

14. Propofol oil-in-water emulsion composition as claimed in claim 1 wherein, said purified natural phosphatide is egg lecithin or soya lecithin.

15. Propofol oil-in-water emulsion composition as claimed in claim 14 wherein, the amount of said purified natural phosphatide is 0.1%-3% w/v.

16. Propofol oil-in-water emulsion composition as claimed in claim 15 wherein, the amount of said purified natural phosphatide is about 1.2% w/v.

17. Propofol oil-in-water emulsion composition as claimed in claim 1 wherein, said tonicity modifying agent is selected from glycerin, dextrose and mannitol.

18. Propofol oil-in-water emulsion composition as claimed in claim 17 wherein, said tonicity modifying agent is glycerin.

19. A composition as claimed in claim 1 wherein, said composition comprises propofol 0.1%-2% w/v; soybean oil up to 30% w/v; purified egg lecithin 0.1%-3% w/v; glycerin about 2.25% w/v; sodium hydroxide sufficient to bring the pH between 6 and 8.5 and water for injection to make up to 100% by volume; and the preservative system consists essentially of monoglyceryl ester of lauric acid 0.001%-0.1% w/v; capric acid and/or its soluble alkaline salts or its monoglyceryl ester (monocaprin) expressed as capric acid 0.001%-0.1% w/v; and disodium edetate nil.

20. A composition as claimed in claim 1 wherein, said composition comprises propofol about 1% w/v; soybean oil about 10% w/v; purified egg lecithin about 1.2% w/v; glycerin about 2.25% w/v; sodium hydroxide sufficient to bring the pH between 6 and 8.5 and water for injection to make up to 100% by volume; and the preservative system consists essentially of monoglyceryl ester of lauric acid about 0.05% w/v; capric acid and/or its soluble alkaline salts or its monoglyceryl ester (monocaprin) expressed as capric acid about 0.05% w/v; and disodium edetate about 0.001% w/v.

21. A composition as claimed in claim 20, wherein the amount of monoglyceryl ester of lauric acid is about 0.05% w/v; capric acid and/or its soluble alkaline salts or its monoglyceryl ester (monocaprin) expressed as capric acid is about 0.025% w/v; and disodium edetate about 0.001% w/v.

22. A composition as claimed in claim 20, wherein the amount of monoglyceryl ester of lauric acid is about 0.025% w/v; capric acid and/or its soluble alkaline salts or its monoglyceryl ester (monocaprin) expressed as capric acid is about 0.05% w/v; and disodium edetate about 0.001% w/v.

23. A composition as claimed in claim 1, wherein the amount of monoglyceryl ester of lauric acid is about 0.05% w/v; capric acid and/or its soluble alkaline salts or its monoglyceryl ester (monocaprin) expressed as capric acid is about 0.05% w/v; and disodium edetate is nil.

24. A composition as claimed in claim 20, wherein the amount of monoglyceryl ester of lauric acid is about 0.05% w/v; capric acid and/or its soluble alkaline salts or its monoglyceryl ester (monocaprin) expressed as capric acid is about 0.025% w/v; and disodium edetate is about 0.0025% w/v.

25. A composition as claimed in claim 20, wherein the amount of monoglyceryl ester of lauric acid is about 0.05% w/v; capric acid and/or its soluble alkaline salts or its monoglyceryl ester (monocaprin) expressed as capric acid is about 0.025% w/v; and disodium edetate is about 0.001% w/v.

26. A composition as claimed in claim 20, wherein the amount of monoglyceryl ester of lauric acid is about 0.025% w/v; capric acid and/or its soluble alkaline salts or its monoglyceryl ester (monocaprin) expressed as capric acid is about 0.025% w/v; and disodium edetate is about 0.0025% w/v.

27. A composition as claimed in claim 20, wherein the amount of monoglyceryl ester of lauric acid is about 0.05% w/v; capric acid and/or its soluble alkaline salts or its monoglyceryl ester (monocaprin) expressed as capric acid is nil; and disodium edetate is about 0.0025% w/v.

28. A composition as claimed in claim 1, wherein the amount of monoglyceryl ester of lauric acid is about 0.025% w/v; capric acid and/or its soluble alkaline salts or its monoglyceryl ester (monocaprin) expressed as capric acid is nil; and disodium edetate is about 0.0025% w/v.

29. A composition as claimed in claim 1, wherein the amount of monoglyceryl ester of lauric acid is about 0.025% w/v, capric acid and/or its soluble alkaline salts or its monoglyceryl ester (monocaprin) expressed as capric acid is about 0.025% w/v.; and disodium edetate is nil.

30. A composition as claimed in claim 20, wherein the amount of monoglyceryl ester of lauric acid is about 0.1% w/v, capric acid and/or its soluble alkaline salts or its monoglyceryl ester (monocaprin) expressed as capric acid is about 0.025% w/v.; and disodium edetate is nil.

31. A composition as claimed in claim 20, wherein the amount of monoglyceryl ester of lauric acid is about 0.05% w/v, capric acid and/or its soluble alkaline salts or its monoglyceryl ester (monocaprin) expressed as capric acid is nil; and disodium edetate is about 0.001% w/v.

32. A process of preparing a composition as claimed in claim 1, comprising:
   i) preparing oil phase in triglyceride oil maintained at about 75° C., by adding propofol;
   ii) preparing an aqueous phase in water at about 70° C.; by adding glycerol and sodium hydroxide solution to make it alkaline;
   iii) adding the emulsifier and individual ingredients of the preservative system of claim 1 in the oil phase either totally or partly and adding the remaining in the aqueous phase;
   iv) adding said oily phase obtained at step i) to said aqueous phase obtained at step ii) under stirring to produce a coarse emulsion;
   v) homogenizing the said coarse emulsion obtained at step iv) to an average globule size of less than 500 nanometers;
   vi) filtering the said composition obtained at the end of step v);
   vii) filling the said filtrate obtained at the end of step vi) in containers such as vials, ampoules, under nitrogen blanketing and sealing the filled containers;
   viii) sterilising said filtrate in said sealed containers by autoclaving.

33. A process of preparing a composition as claimed in claim 32, comprising:
   i) preparing oil phase in triglyceride oil maintained at about 75° C., by dissolving propofol and the emulsifier;
   ii) preparing an aqueous phase in water at about 70° C.; by adding glycerol, sodium hydroxide solution;
   iii) adding said oily phase obtained at step i) to said aqueous phase obtained at step ii) under stirring to produce a coarse emulsion;
   iv) homogenizing the said coarse emulsion obtained at step iii) to an average globule size of less than 500 nanometers;
   v) adding the chosen preservative system as claimed in any preceding claim;
   vi) filtering the said composition obtained at the end of step v);
   vii) filling the said filtrate obtained at the end of step vi) in containers such as vials, ampoules, under nitrogen blanketing and sealing the filled containers;
   viii) sterilising said filtrate in said sealed containers by autoclaving.

34. A process of preparing a composition as claimed in claim 33 wherein, the chosen preservative system comprises monoglyceryl ester of lauric acid (monolaurin) about 0.05% w/v and capric acid about 0.05% w/v of the emulsion composition and containing no edetate.

\* \* \* \* \*